United States Patent [19]

Müller et al.

[11] Patent Number: 5,424,479

[45] Date of Patent: Jun. 13, 1995

[54] PROCESS FOR THE PREPARATION OF AROMATIC METHYL METHOXYCARBOXYLATES

[75] Inventors: Rolf Müller, Karben-Rendel; Thomas Wessel, Frankfurt am Main, both of Germany

[73] Assignee: Cassella AG, Frankfurt, Germany

[21] Appl. No.: 294,449

[22] Filed: Aug. 23, 1994

[30] Foreign Application Priority Data

Aug. 31, 1993 [DE] Germany .................... 43 29 286.0

[51] Int. Cl.[6] ........................................... C07C 69/76
[52] U.S. Cl. ........................................ 560/64; 560/56
[58] Field of Search .................................. 560/64, 56

[56] References Cited

U.S. PATENT DOCUMENTS 1,930,135 10/1933 Smith et al. ..................... 560/64

Primary Examiner—Paul J. Killos
Attorney, Agent, or Firm—Connolly & Hutz

[57] ABSTRACT

The invention relates to a preparation process for aromatic methyl methoxycarboxylates by reaction of aromatic hydroxycarboxylic acids in the form of a mixture with the methoxycarboxylic acids with dimethyl sulphate in water.

20 Claims, No Drawings

PROCESS FOR THE PREPARATION OF AROMATIC METHYL METHOXYCARBOXYLATES

The present invention relates to a process for the preparation of aromatic methyl methoxycarboxylates by a methylation reaction using dimethyl sulphate in aqueous solution.

Aromatic methoxycarboxylates are used widely as valuable synthesis units, for example as intermediates for pharmaceuticals or as components of polyesters. For example, methyl 6-methoxy-1-naphthoate is an important intermediate in the synthesis of the pharmacological active substance tolrestat, a pharmaceutical for preventing and treating sequelae of diabetes mellitus (see, for example, EP-B-59 596, EP-B-200 840, EP-A-307 519, U.S. Pat. No. 4,808,748). Another example is methyl 3-methoxy-4-methylbenzoate, which is a valuable intermediate for pharmaceutical preparations (see, for example, EP-B-83 228).

A generally applicable process for the preparation of carboxylates is alkylating the salts of the carboxylic acids using dialkyl sulphates, that is to say dimethyl sulphate for the preparation of the methyl esters, see, for example, Houben-Weyl-Müller, Methoden der Organischen Chemie [Methods in Organic Chemistry], 4th Edition, Volume 8, pp. 541–543. Equally, the etherification of phenols with dialkyl sulphates is a recognized process for the preparation of alkoxy aromatics, in particular the etherification using dimethyl sulphate is a preparation process for methoxy aromatics, see, for example, Houben-Weyl-Müller, Methoden der Organischen Chemie [Methods in Organic Chemistry], 4th Edition, Volume 6/3, pp. 62–66.

The simultaneous or multi-step alkylation of the hydroxyl group and the carboxyl group in phenol carboxylic acids is a useful process for the preparation of aromatic alkyl alkoxycarboxylates if the aromatic hydroxycarboxylic acids are readily accessible, in particular of methyl methoxycarboxylates, dimethyl sulphate also being suitable as methylating agent. Reactions of phenol carboxylic acids with dialkyl sulphates and, in particular, dimethyl sulphate are described, for example, in Organikum [Laboratory Practical in Organic Chemistry], 15th Edition, VEB Deutscher Verlag der Wissenschaften, pp. 251–253, or Houben-Weyl-Müller, see above, Volume 6/3, pp.62–66. In such reactions of phenol carboxylic acids with dimethyl sulphate, the more reactive phenolic hydroxyl group generally reacts more rapidly than the carboxyl group. If it is only the hydroxyl group which is to be methylated, this process is frequently acceptable, even though, as a rule, product mixtures result.

If it is intended to achieve complete methylation, both on the hydroxyl group and on the carboxyl group, then the known processes for the conversion of phenol carboxylic acids into methyl methoxycarboxylates are generally not suitable for an industrial scale process. A particular disadvantage is the excess of dimethyl sulphate which must be employed for a substantial extent of methylation and which is generally very large and has to be removed or destroyed in a complicated procedure after the reaction, while the by-products which are present despite, or else because of, the large excess frequently require laborious and expensive product purification steps, so that the yield achieved is uneconomically low.

For example, the methylation of gallic acid, which is described in the Monatshefte für Chemie, Volume 91, p. 1077 et. seq. (1960), results in a yield of complete methylation product of only 75%, despite the use of 6.4 times the molar amount of dimethyl sulphate based on the number of moles of hydroxyl and carboxyl groups to be reacted. The preparation of methyl 6-methoxy-1-naphthoate described in EP-B-200 840 employs 3.4 times the molar amount of dimethyl sulphate based on the total number of moles of hydroxyl and carboxyl groups to be methylated in the 6-hydroxy-1-naphthoic acid/6-methoxy-1-naphthoate acid mixture employed, which has been obtained in this form from the previous reaction step in this process. Moreover, the process only yields a product of low purity (87%; see Comparison Example 1). The methylation of hydroxy naphthoic acids mentioned in the Berichte der Deutschen Chemischen Gesellschaft, Volume 37, p. 3658 et. seq. (1904) uses twice the molar amount of dimethyl sulphate based on the number of moles of groups to be methylated and only gives a yield of 70% of the desired product.

Known processes in which small excesses are employed are distinguished by other disadvantages which prevent their use on an industrial scale or which would require complicated, complex apparatus for ecological or safety reasons. For example, the preparation of methyl 2-methoxybenzoate described in the Berichte der Deutschen Chemischen Gesellschaft, Volume 40, p. 714 et. seq. (1907), in which all of the starting substances are combined and heated, is not reproducible because of the uncontrolled reaction procedure which starts at high temperatures and cannot be scaled up to an industrial scale. In the preparation of methyl 6-methoxy-1-naphthoate described in U.S. Pat. No. 4,590,290, only 1.2 mol of dimethyl sulphate are used per mole of hydroxyl and carboxyl groups to be methylated in the 6-hydroxy-1-naphthoic acid employed, but a yield of only 78% of a product of only 93% purity is obtained despite complicated purification processes, and, in particular, the reaction is carried out in butyl acetate as a solvent, whose use on an industrial scale requires extensive measures for protecting the plant against fire and explosion and for exhaust air purification. This also applies if the solvents used in the methylation processes are, for example, dioxane, acetone or methanol. 1,2-dichloroethane, which is used as a solvent component in the process described in EP-B-200 840, in which water is only mentioned as a solvent but not used in the examples, is, moreover, to be avoided especially on work hygiene grounds, because of its toxological properties.

There is therefore a demand for a process for the preparation of aromatic methyl methoxycarboxylates, which can be carried out simply, on an industrial scale and without organic solvents, which avoids the uneconomically high excesses of methylating agent used in known methylation processes of aromatic hydroxycarboxylic acids.

Surprisingly, it has been found that this object is achieved by reacting aromatic hydroxycarboxylic acids in the form of a mixture with the corresponding methoxycarboxylic acids in water with only 0.8 to 1.7 times the molar amount of dimethyl sulphate relative to the total number of moles of hydroxyl and carboxyl groups to be methylated in the starting substances. A particularly large amount of the dimethyl sulphate is utilized, and very pure products are obtained in high yield without complicated work-up and purification steps being necessary.

The invention therefore relates to a process for the preparation of aromatic methyl methoxycarboxylates of the general formula I $$CH_3O-Ar-COOCH_3 \quad (I)$$

in which Ar is a phenylene radical or a naphthylene radical, it also being possible for the phenylene radical to be mono- or disubstituted and for the naphthylene radical to be mono-, di- or trisubstituted by halogen atoms, $(C_1-C_4)$alkyl groups, $(C_2-C_5)$alkenyl groups, $(C_1-C_4)$alkoxy groups, benzyloxy groups, trifluoromethyl groups, nitro groups, hydroxymethyl groups, formyl groups, cyano groups and $((C_1-C_4)$alkoxy)carbonyl groups, by reacting aromatic hydroxycarboxylic acids of the general formula II $$HO-Ar-COOH \quad (II)$$

in a mixture with aromatic methoxycarboxylic acids of the general formula III $$CH_3O-Ar-COOH \quad (III)$$

where Ar in II and III is as defined for I, with dimethyl sulphate in the presence of a base, characterized in that the reaction is carried out in water and in that 0.8 to 1.7 times the molar amount of dimethyl sulphate based on the total number of moles of hydroxyl and carboxyl groups to be methylated in the starting substances is employed.

Examples of hydroxy carboxylic acids from which, in the form of a mixture with the corresponding methoxycarboxylic acids, methyl methoxycarboxylates are thus to be prepared by the process according to the invention are 2-hydroxy-, 3-hydroxy- and 4-hydroxybenzoic acids and 1-hydroxy-, 2-hydroxy-, 3-hydroxy-, 4-hydroxy-, 5-hydroxy-, 6-hydroxy-, 7-hydroxy- and 8-hydroxy-1-naphthoic acids and -2-naphthoic acids. In the case of the benzoic acid derivatives, the aromatic can, besides the hydroxyl or methoxy group and the carboxyl or methoxycarbonyl group, additionally have one or two further substituents and, in the case of the naphthoic acid derivatives, additionally one, two or three further substituents, it being possible for the substituents to be in any position and, in the case of the naphthoic acid, to be distributed to both rings, and it being possible for the substituents to be identical in all or some cases or to differ from each other in all cases.

Examples of halogen atoms which can form substituents on the benzene or naphthalene ring system are fluorine, chlorine, bromine and iodine. Examples of $(C_1-C_4)$alkyl groups are the methyl, ethyl, n-propyl, i-propyl, n-butyl, i-butyl, s-butyl and t-butyl radical, examples of $C_2-C_5$ alkenyl groups are the vinyl, allyl, 2-methylallyl, 2-butenyl, 1,1-dimethylallyl and 4-methyl-2-butenyl radical. Examples of $(C_1-C_4)$alkoxy groups which can occur as substituents are the methoxy, ethoxy, n-propoxy, i-propoxy, n-butoxy, i-butoxy and t-butoxy radical. Examples of $((C_1-C_4)$alkoxy)carbonyl groups are the methoxycarbonyl, ethoxycarbonyl, i-propoxycarbonyl, n-butoxycarbonyl, i-butoxycarbonyl and t-butoxycarbonyl radical.

The process according to the invention preferably embraces the preparation of aromatic methyl methoxycarboxylates of the general formula Ia $$CH_3O-Ar^1-COOCH_3 \quad (Ia)$$

in which $Ar^1$ is a 3-phenylene radical or a 4-phenylene radical which has no further substituents or which has, as further substituents, one or two additional $(C_1-C_4)$alkyl groups, from the corresponding 3-hydroxy- and 4-hydroxybenzoic acids in the form of a mixture with the methoxy acids. Particularly preferred is the preparation of compounds of the general formula Ib $$CH_3O-Ar^2-COOCH_3 \quad (Ib)$$

in which $Ar^2$ is a 3-phenylene radical or a 4-phenylene radical which has, as further substituents, two or, preferably, one additional methyl group, from the corresponding 3-hydroxy- and 4-hydroxybenzoic acid in the form of a mixture with the methoxy acids. Additionally preferred is the preparation of methyl 3-methoxy-4-methylbenzoate from 3-hydroxy-4-methylbenzoic acid in the form of a mixture with 3-methoxy-4-methylbenzoic acid.

Another preferred embodiment of the process according to the invention embraces the preparation of aromatic methyl methoxycarboxylates of the general formula Ic $$CH_3O-Ar^3-COOCH_3 \quad (Ic)$$

in which $Ar^3$ is a naphthylene radical which has no further substituents or, as further substituents, one or two additional $(C_1-C_4)$alkyl groups, preferably methyl groups, from the corresponding hydroxynaphthoic acids in the form of a mixture with the methoxynaphthoic acids. Particularly preferred is the preparation of compounds of the general formula Id $$CH_3O-Ar^4-COOCH_3 \quad (Id)$$

in which $Ar^4$ is 1,4- or 1,5- or 1,6- or 1,7- or 1,8- or 2,4- or 2,5- or 2,6- or 2,7- or 2,8-naphthylene radical which has no further substituents, from the corresponding hydroxy-1-naphthoic acid or hydroxy-2-naphthoic acid in the form of a mixture with the methoxynaphthoic acid. Additionally preferred is the preparation of methyl 6-methoxy-1-naphthoate from 6-hydroxy-1-naphthoate in the form of a mixture with 6-methoxy-1-naphthoic acid.

The aromatic hydroxycarboxylic acids and methoxycarboxylic acids used as starting material are known or are accessible by known preparation processes. For example, 6-methoxy-1-naphthoic acid is described in Liebigs Annalen der Chemie, Volume 188, p. 8 (1877), in the journal of the Chemical Society, Volume 123, p. 1641 (1923) or in EP-B-268 088, and 6-methoxy-1-naphthoic acid in the Journal of the American Chemical Society, Volume 69, p. 2261 (1947). 3-Hydroxy-4-methylbenzoic acid is described, for example, in Berichte der Deutschen Chemischen Gesellschaft, Volume 6, p. 481 (1873), 3-methoxy-4-methylbenzoic acid in Helvetica Chimica Acta, Volume 19, p. 370 (1936) or in the Journal of the Chemical Society, Volume 119, p. 1342 (1921). The acid mixture which is methylated in the reaction according to the invention may have been obtained from hydroxycarboxylic acid and methoxycarboxylic acid, each of which has previously been isolated, but may also have been already obtained as a mixture in the previous synthesis step, such as, for example, in the case of EP-B-200 840, which has already been mentioned.

When carrying out the process according to the invention, the amount of methoxycarboxylic acid of the general formula III, which is reacted with dimethyl sulphate in the form of a mixture with the hydroxycarboxylic acid of the general formula II, is, per se, arbitrary. It is preferred to react mixtures which contain up to 2 mol of the corresponding methoxycarboxylic acid of the general formula III per mole of hydroxycarboxylic acid of the general formula II, that is to say, for example, 0.01 to 2 mol or 0.05 to 2 mol per mole of hydroxycarboxylic acid, or else, for example, 0.01 to 1 mol or 0.05 to 1 mol per mole of hydroxycarboxylic acid. A particularly favourable ratio will depend on each individual case. In the particularly preferred preparation of methyl 6-methoxy-1-naphthoate, it is particularly preferred to react a mixture which contains 0.1 to 1 mol, more preferably 0.3 to 0.8 mol, of 6-methoxy-1-naphthoic acid per mole of 6-hydroxy-1-naphthoic acid. In the preparation of methyl 3-methoxy-4-methylbenzoate, which is also particularly preferred, it is particularly preferred to react a mixture which contains 0.05 to 1 mol, moreover preferably 0.1 to 0.4 mol, of 3-methoxy-4-methylbenzoic acid per mole of 3-hydroxy-4-methylbenzoic acid.

In a preferred embodiment, all or some, particularly preferably all, of the methoxycarboxylic acid of the general formula III in the carboxylic acid mixture to be reacted is derived from one or more previous reactions by the process according to the invention. Depending on the reaction conditions, which depend on each individual case, some of the carboxyl groups in the acids employed are not methylated, with the exception of the product of complete methylation, the compound of the general formula I, that is to say various amounts of the methoxy carboxylic acid of the general formula III can again be obtained as a by-product of the reaction. This methoxycarboxylic acid of the general formula III can readily be separated from the methyl ester of the general formula I by the principle of pH separation.

For example, to work up the reaction mixture, the completely methylated product of the general formula I which does not form salts can be separated by filtration, centrifugation, separation of a liquid phase, extraction or another customary process suitable for the individual case, at a suitable pH which will generally be in the alkaline range, at which the compound of the general formula III is in salt form, and the compound of the general formula III which is not completely methylated can subsequently be converted into the form of the free acid which can readily be isolated, for example by acidification to a suitable pH at which the compound of the general formula III is in the form of the free acid, and this compound which is not completely methylated can then be separated from the aqueous solution by a suitable customary process. The methoxycarboxylic acid of the general formula III which has been reisolated is generally so pure that it can be added to the aromatic hydroxycarboxylic acid of the general formula II to be methylated in a subsequent batch without an additional purification operation.

The amount of the methoxycarboxylic acid of the general formula III which is isolated in addition to the completely methylated product in each batch in a series of subsequent batches in accordance with the preferred embodiment and again added to the next batch depends on the structure of the compounds and on the reaction conditions and can, of course, vary from batch to batch to a certain extent, but is constant to a large extent when a suitable amount of dimethyl sulphate and suitable reaction conditions are selected. As described above, the hydroxycarboxylic acids of the general formula II can also be reacted on their own without an addition of the methoxycarboxylic acids of the general formula III, or the methoxycarboxylic acids of the general formula III can be reacted on their own without an addition of the hydroxycarboxylic acids of the general formula II. If it is intended to start a sequence of batches in accordance with the preferred embodiment, in which the acid of the general formula III is derived from previous reactions, starting with only the hydroxy acid of the general formula II, then this hydroxy acid is reacted with 0.8 to 1.7 times the molar amount of dimethyl sulphate based on the total number of moles of hydroxyl and carboxyl groups to be methylated, in water in the presence of a base. The same applies analogously when it is intended to prepare more methyl ester of the general formula I from the last methoxy acid of the general formula III which has been isolated from a sequence of batches in accordance with the preferred embodiment, without again adding more hydroxy acid.

The procedure for carrying out the process according to the invention and the reaction conditions depend on each individual case. Conventionally, water, the base or some of the base and the substance to be methylareal, i.e. the hydroxycarboxylic acid of the general formula II in the form of a mixture with the methoxycarboxylic acid of the general formula III, are introduced into the reaction vessel and, if appropriate, the reaction mixture is brought to the desired temperature, and the dimethyl sulphate is then metered in in portions or continuously at the desired temperature over a specific period which will depend on each individual case and, if appropriate, more base is also metered in, it being possible to maintain a pH range which is particularly favourable for each individual case, in particular by metering in the base. Hydrolysis of the dimethyl sulphate is only a minor occurrence in this procedure. However, the reaction can also be carried out in such a manner that, for example, the total amount or some of the dimethyl sulphate in the form of a mixture with water is introduced, and the material to be methylated and the base are metered in over a specific period at the desired temperature, for example in the form of an aqueous solution of the salt of the carboxylic acid to be employed which has been prepared with the base, it being possible here, again, for the base to be metered in in such a manner that a particularly favourable pH range is maintained. In this case, the reaction proceeds in a two-phase system from the beginning. If appropriate, more dimethyl sulphate and more base are metered in after the carboxylic acids have been metered in. Moreover, the reaction can, for example, also be carried out in a flow reactor into whose reaction chamber the dimethyl sulphate and also the substance to be methylareal and the base are metered at the desired temperature, it being possible, again, to add more dimethyl sulphate and base to the reaction mixture at a later point in time, if desired. In all these cases, process control of the reaction allows defined reaction conditions to be maintained which are particularly favourable for the individual case. This results in a reproducible, high degree of utilization of the dimethyl sulphate. Depending on the individual case, an amount of dimethyl sulphate of 1.0 to 1.7 mol or 1.0 to 1.6 mol or 1.0 to 1.5 mol, based on the total number of moles of hydroxyl and carboxyl groups to be methylated in the starting substances, may also be preferred. In the case of the preparation of methyl 6-methoxy-1-naphthoate, it is preferred to employ 1.0 to 1.3 times, particularly preferably 1.0 to 1.1 times, the molar amount of dimethyl sulphate, based on the total number of moles of hydroxyl and carboxyl groups to be methylated in the 6-hydroxy- and 6-methoxy-1-naphthoic acid.

The reaction temperature and the pH at which the methylation according to the reaction is carried out depend on the reactivities of the hydroxyl and carboxyl groups which are determined by the structure of the substrate and on the tendency of the methoxycarbonyl group which forms and of the dimethyl sulphate to hydrolyse and thus depend on the individual case. The nature of the base which is added also has an effect. When carrying out the process without pressure, reaction temperatures up to the boiling point of the reaction mixture may be appropriate. The reaction is preferably carried out between 10° and 90° C., particularly preferably between room temperature and 70° C., very particularly preferably between 30° and 60° C. The temperature can also be altered during the reaction, for example it may be increased towards the end of the reaction. The reaction can be carried out not only without pressure, but also under pressure, for example the inherent pressure which is established in a closed system.

Depending on each individual case, all of the base can be introduced at the beginning of the reaction and the pH can subsequently remain unaffected or it is possible to introduce some of the base at the beginning and then later to maintain a certain pH range by an addition of more base, or the entire course of the reaction can be carried out with the pH being checked. In order to achieve optimum conversion rates and degrees of utilization of the dimethyl sulphate, it may be appropriate to alter the pH range during the course of the reaction, for example first to meter in some of the dimethyl sulphate in a higher range and then some more in a lower pH range, but, equally, the reverse procedure may be appropriate. In general, the reaction is carried out in the alkaline range; however, in some cases, a weakly acidic pH can also be appropriate, depending on the structure of the substrate. In one embodiment of the process according to the invention, for example, pH values of between 8 and 12 are favourable during the pH check phase in the preparation of methyl 6-methoxy-1-naphthoate.

Suitable bases for use in the process according to the invention are all those which do not engage in troublesome side-reactions under the reaction conditions, in particular those which are not methylated by dimethyl sulphate. Inorganic bases are preferably employed, but other bases which can be employed are, for example, tetrasubstituted ammonium hydroxides, sterically hindered amines, alcoholates, such as sodium methylate, sodium ethylate, sodium tert-butylate, potassium methylate, potassium ethylate or potassium tert-butylate, or suitable ion exchangers. Particularly preferred are alkali metal hydroxides, alkali metal carbonates, alkaline earth metal hydroxides and alkaline earth metal carbonates, possible alkaline earth metals and alkali metals being, in particular, calcium, barium, lithium, sodium, potassium and caesium. Additionally preferred are alkali metal hydroxides, such as lithium hydroxide, sodium hydroxide, potassium hydroxide or caesium hydroxide, amongst these especially sodium hydroxide and potassium hydroxide, and most of all potassium hydroxide. The use of mixtures of a plurality of bases may also be advantageous, for example sodium hydroxide together with potassium hydroxide or potassium carbonate together with potassium hydroxide. The base or the bases can be applied in pure form or, which is commercially more available, as a solid, or in the form of aqueous solutions. When selecting the base, the solubility properties of the salts in the reaction mixture are also to be taken into account. The amount of base to be employed depends on each individual case and is affected, for example, by the choice of the pH range, or pH ranges, in which the reaction is carried out. In total, a molar amount of base equivalents is required at least such that the total number of moles of hydroxyl and carboxyl groups in the hydroxy- and methoxycarboxylic acids to be reacted can be deprotonated, but, in general, an excess amount of base is added.

Possible ways of work-up of the reaction mixture obtained when carrying out the process according to the invention have already been mentioned. Work-up can be effected by isolation or separation methods known per se, for example by filtration, centrifugation, phase separation, extraction, distillation (in vacuo) or steam distillation, or else by chromatographic methods, in particular by utilizing the principle of pH separation. Addition of a base after the reaction has ended allows a suitable pH to be established at which the methoxycarboxylic acid of the general formula III is in salt form. Due to the different physical properties, in particular the solubility, the completely methylated methyl methoxycarbonate of the general formula I which is not capable of salt formation can readily be separated from the methoxycarboxylic acids of the general formula III. The latter can subsequently be converted, as has already been mentioned, from the salt form to the form of the free acid for example by addition of acid, for example hydrochloric acid or sulphuric acid, until a suitable pH has been reached, and the free acid can then be isolated, equally by methods known per se, such as filtration, centrifugation, extraction, phase separation, and, if appropriate, also after concentration, or concentration to some extent, of the water phase. Alternatively, the methoxycarboxylic acids of the general formula III can be obtained for example by salting out or by extracting their salts. In general, they can be employed directly in a subsequent batch, even without drying.

The desired methyl methoxycarboxylates of the general formula I are obtained in very high purity in the process according to the invention, so that complicated purification steps are generally not necessary. If the compound of the general formula I is a solid, it is generally sufficient to wash the isolated product with water and to dry it. In the case of liquid compounds of the general formula I, a simple distillation (in vacuo) can be carried out after the product phase has been separated off so as to remove any remaining water or salt. If further purification should be required for specific uses, this can be carried out by methods known per se, for example by recrystallization, distillation, sublimation or by chromatography.

EXAMPLE 1

188 g (1.00 mol) of 6-hydroxy-1-naphthoic acid and 115 g (0.57 mol) of 6-methoxy-1-naphthoic acid together with 154 g (2.75 mol) of potassium hydroxide are dissolved in 700 ml of water. 130 g (1.03 mol) of dimethyl sulphate are subsequently added dropwise at 40° C., the pH being kept between 10.6 and 11.0 by an addition of KOH. 210 g (1.67 mol) of dimethyl sulphate are then added dropwise while the pH drops, the pH being kept at 8.8–9 by an addition of KOH. Stirring is continued, and the pH is subsequently brought to 12 using KOH so as completely to dissolve the 6-methoxy-1-naphthoic acid. The crude ester is separated off, washed and distilled in vacuo. The aqueous phase is acidified, and the 6-methoxy-1-naphthoic acid is isolated by filtration and again added to the next batch (final weight: 115 g, dry).

Yield: 208 g (96%, based on 6-hydroxy-1-naphthoic acid employed) (the total yield of methyl 6-methoxy-1-naphthoate and 6-methoxy-1-naphthoic acid, based on the mixture of 6-hydroxy- and 6-methoxy-1-naphthoic acid employed, is 98%) Pure substance content: >99% (GC) Melting point: 44° C.

Comparison Example 1 (in accordance with Example 1 of EP-B-200840)

56 g (0.5 mol) of furan-2-carboxylic acid and 270 g (2.5 mol) of anisole are dissolved in 190 ml of o-dichlorobenzene. 270 g (2.0 mol) of anhydrous aluminium chloride (30 portions of 9 g each) are subsequently added at 40° C. in the course of 5 hours. After the addition has ended, the mixture is diluted with 70 ml of o-dichlorobenzene and 100 g (0.93 mol) of anisole, stirring is continued for 3.5 hours, and the reaction mixture is hydrolysed by stirring it for 1 hour with 1500 ml of 6N hydrochloric acid. After phase separation, the aqueous phase is extracted using 250 ml of isopropyl acetate, and a total of approximately 950 g of organic phase is obtained which contain approximately 0.12 mol of 6-methoxynaphthoic acid and 0.06 mol of 6-hydroxynaphthoic acid. The organic phase is extracted at 60° C. using 400 ml of saturated potassium hydrogen carbonate solution, the pH of the aqueous phase is brought to 1 using hydrochloric acid, and the 6-hydroxy/methoxy-1-naphthoic acids obtained are dissolved in 300 ml of 1,2-dichloroethane. 78 ml (0.82 mol) of dimethyl sulphate, 108 g (0.78 mol) of potassium carbonate and 500 ml of acetone are subsequently added and the mixture is stirred for 3 hours at approximately 60° C. The solvents acetone and dichloroethane are then distilled off, and the methyl 6-methoxy-1-naphthoate which remains is distilled in vacuo.

Yield: 34.5 g (77%) Pure substance content: 87% (GC) Melting point: viscous liquid, solidifies occasionally (35°–40° C.)

In the table which follows, the process according to the invention and the prior art for the preparation of methyl 6-methoxy-1-naphthoate are again compared.

| | According to the invention Example 1 | EP-B-200840 I[1] | Prior Art II[1] | US 4590290 |
|---|---|---|---|---|
| Solvent | Water | Acetone/Water | Dichloroethane/Acetone | Butyl acetate |
| Amount of DMS[2] | 1.05 | 3.4 | 3.4 | 1.2 |
| Degree of utilization of dimethyl sulphate | 74% | 20% | 23% | 66% |
| Yield of pure substance | 96%[3] | 69%[4] | 77% | 78% |

| | According to the invention Example 1 | EP-B-200840 I[1] | Prior Art II[1] | US 4590290 |
|---|---|---|---|---|
| Purity | >99% | | 87% | 93% |

[1]I: Example 4 of EP-B-200840; II: Comparison Example 1 of the present text in which Example 1 of EP-B-200 840 was reproduced.
[2]Amount of dimethyl sulphate in mol, based on the total number of moles of hydroxyl and carboxyl groups to be methylated in the starting material.
[3]Based on 6-hydroxy-naphthoic acid employed; the total yield of methyl 6-methoxy-1-naphthoate and 6-methoxy-1-naphthoic acid based on the mixture of 6-hydroxy- and 6-methoxy-1-naphthoic acid employed is 98%.
[4]Crude yield, since no information on purity.

EXAMPLE 2

55.8 g (0.37 mol) of 3-hydroxy-4-methylbenzoic acid and 13.5 g (0.08 mol) of 3-methoxy-4-methylbenzoic acid together with 55.8 g (1.0 mol) of potassium hydroxide are dissolved in 300 ml of water. 147 g (1.16 mol) of dimethyl sulphate are subsequently added dropwise at 40° C. in the course of approximately 3 hours, the pH being kept at 10.8–11 by an addition of KOH. Stirring is then continued for another 30 minutes, and the ester separated off, washed with water and dried in vacuo. The aqueous phase is acidified, and the 3-methoxy-4-methylbenzoic acid is isolated by filtration and again added to the next batch (final weight: 13.5 g, dry).

Yield: 64.3 g (97%, based on 3-hydroxy-4-methylbenzoic acid employed) (the total yield of methyl 3-methoxy-4-methylbenzoate and 3-methoxy-4-benzoic acid, based on the mixture of 3-hydroxy- and 3-methoxy-4-methylbenzoic acid employed, is 98%) Pure substance content: >99.5% (GC) Melting Point: 51° C.

EXAMPLE 3

Preparation of methyl 3,5-dichloro-4-methoxybenzoate by methylation of a mixture of 3,5-dichloro-4-hydroxybenzoic acid and 3,5-dichloro-4-methoxybenzoic acid.

76.6 g (0.37 mol) of 3,5-dichloro-4-hydroxybenzoic acid and 28.7 g (0.13 mol) of 3,5-dichloro-4-methoxybenzoic acid (from the previous batch) together with 67 g of 85% potassium hydroxide are dissolved in 350 ml of water. 155 g (1.22 mol) of dimethyl sulphate are subsequently added dropwise at 40° C. in the course of 3 hours, the pH being maintained at 11.5 by an addition of potassium hydroxide. After the addition has ended, stirring is continued for 30 minutes, and methyl 3,5-dichloro-4-methoxybenzoate, which has precipitated, is filtered off with suction, washed with water and dried in vacuo. The aqueous filtrate is acidified, and the 3,5-dichloro-4-methoxybenzoic acid, which has precipitated, is isolated by filtration and dried. 23.9 g of dry 3,5-dichloro-4-methoxybenzoic acid are obtained and again added to the next batch.

Yield of methyl 3,5-dichloro-4-methoxybenzoate: 91.3 g (105%, based on 3,5-dichloro-4-hydroxybenzoic acid employed).

The total yield of methyl 3,5-dichloro-4-methoxybenzoate and 3,5-dichloro-4-methoxybenzoic acid, based on the mixture of 3,5-dichloro-4-hydroxy- and -4-methoxybenzoic acid employed, is 99%. Pure substance content: 97.2% (GC) Melting point: 73°–76° C.

EXAMPLE 4

Preparation of methyl 4-methoxy-3-nitrobenzoate by methylation of a mixture of 4-hydroxy-3-nitrobenzoic acid and 4-methoxy-3-nitrobenzoic acid.

42.1 g (0.23 mol) of 4-hydroxy-3-nitrobenzoic acid and 53.2 g (0.27 mol) of 4-methoxy-3-nitrobenzoic acid (from the previous batch) together with 60 g of 85% potassium hydroxide are dissolved in 550 ml of water. 155 g (1.22 mol) of dimethyl sulphate are subsequently added at 40° C. in the course of 3 hours, the pH being maintained at or above 11 by an addition of 10N KOH solution. After the addition has ended, stirring is continued for 30 minutes, the pH is brought to 13.5, and methyl 4-methoxy-3-nitrobenzoate, which has precipitated, is filtered off with suction. It is washed with water and dried in vacuo. The aqueous filtrate is acidified, and the 4-methoxy-3-nitrobenzoic acid, which has precipitated, is isolated by filtration and dried. 53 g of dry 4-methoxy-3-nitrobenzoic acid are obtained and again added to the next batch.

Yield of methyl 4-methoxy-3-nitrobenzoate: 44.3 g (91.3%, based on 4-hydroxy-3-nitrobenzoic acid employed).

The total yield of methyl 4-methoxy-3-nitrobenzoate and 4-methoxy-3-nitrobenzoic acid, based on the mixture of 4-hydroxy- and 4-methoxy-3-nitrobenzoic acid employed, is 95.8%. Pure substance content: 100% (GC) Melting point: 107° C.

We claim:

1. Process for the preparation of aromatic methyl methoxy carboxylates of the formula (I)

$$CH_3O-Ar-COOCH_3 \quad (I)$$

in which Ar is an unsubstituted or mono- or disubstituted phenylene radical or an unsubstituted or mono-, di- or trisubstituted naphthylene radical, wherein the substituents are selected from the group consisting of halogen atoms, $(C_1-C_4)$alkyl groups, $(C_2-C_5)$alkenyl groups, $(C_1-C_4)$alkoxy groups, benzyloxy groups, trifluoromethyl groups, nitro groups, hydroxymethyl groups, formyl groups, cyano groups and $((C_1-C_4)$alkoxy)carbonyl groups, comprising reacting aromatic hydroxycarboxylic acids of the formula II $$HO-Ar-COOH \quad (II)$$

in a mixture with aromatic methoxycarboxylic acids of the formula III $$CH_3O-Ar-COOH \quad (III)$$

where Ar in formulas II and III are the same as defined for Ar in formula I above, with dimethyl sulphate in the presence of a base, wherein the reaction is carried out in water and in that about 0.8 to about 1.7 times the molar mount of dimethyl sulphate based on the total number of moles of hydroxyl and carboxyl groups to be methylated in the starting substances is employed.

2. The process according to claim 1, wherein the mixture that is reacted contains an mount up to 2 mol of the corresponding methoxycarboxylic acid of the formula III per mole of hydroxycarboxylic acid of the formula II.

3. The process according to claim 1, wherein all or some of the methoxycarboxylic acid of the formula III in the carboxylic acid mixture to be reacted is derived from one or more previous reactions according to claim 1.

4. The process according to claim 1, wherein the reaction is carried out between about 10° and about 90° C.

5. The process according to claim 1, wherein the reaction is carried out between about room temperature and about 70° C.

6. The process according to claim 1, wherein the reaction is carried out between about 30° and about 60° C.

7. The process according to claim 1, wherein the reaction is carried out in the presence of an alkali metal hydroxide.

8. The process according to claim 7, wherein said alkali metal hydroxide is sodium hydroxide or potassium hydroxide.

9. The process according to claim 1, wherein 6-hydroxy-1-naphthoic acid in the form of a mixture with 6-methoxy-1-naphthoic acid is reacted to give methyl 6-methoxy-1-naphthoate.

10. The process according to claim 9, wherein the reaction mixture contains, about 0.1 to about 1 mol of 6-methoxy-1-naphthoic acid per mole of 6-hydroxy-1-naphthoic acid.

11. The process according to claim 10, wherein the reaction mixture; contains about 0.3 to about 0.8 mol of 6-methoxy-1-naphthoic acid per mole of 6-hydroxy-1-naphthoic acid.

12. The process according to claim 9, wherein about 1.0 to about 1.3 times, the molar mount of dimethyl sulphate, based on the total number of moles of hydroxyl and carboxyl groups in the 6-hydroxy- and 6-methoxy-1-naphthoic acid to be methylated, is employed.

13. The process according to claim 12, wherein about 1.0 to about 1.1 times, the molar mount of dimethyl sulphate, based on the total number of moles of hydroxyl and carboxyl groups in the 6-hydroxy- and 6-methoxy-1-naphthoic acid to be methylated, is employed.

14. The process according to claim 1, wherein 3-hydroxy-4-methylbenzoic acid in the form of a mixture with 3-methoxy-4-methylbenzoic acid is reacted to give methyl 3-methoxy-4-methylbenzoate.

15. The process according to claim 14, wherein a mixture is reacted which contains about 0.05 to about 1 mol of 3-methoxy-4-methylbenzoic acid per mole of 3-hydroxy-4-methylbenzoic acid.

16. The process according to claim 14, wherein a mixture is reacted which contains about 0.1 to about 0.4 mol of 3-methoxy-4-methylbenzoic acid per mole of 3-hydroxy-4-methylbenzoic acid.

17. The process as claimed in claim 1, wherein Ar is a substituted or unsubstituted 3-phenylene radical or a 4-phenylene radical.

18. The process as claimed in claim 1, wherein Ar is a substituted or unsubstituted 3-phenylene radical.

19. The process as claimed in claim 1, wherein Ar is a substituted or unsubstituted naphthylene radical.

20. The process as claimed in claim 19, wherein Ar is a 1,4- or 1,5- or 1,6-, or 1,7- or 1,8- or 2,4- or 2,5- or 2,6- or 2,7- or 2,8-naphthylene radical.

* * * * *